US011896502B2

(12) United States Patent
Shen

(10) Patent No.: US 11,896,502 B2
(45) Date of Patent: *Feb. 13, 2024

(54) ADJUSTABLE PROSTHESIS LEG

(71) Applicant: Ossur Iceland ehf, Reykjavik (IS)

(72) Inventor: Hsin-Fa Shen, Banqiao (TW)

(73) Assignee: Ossur Iceland ehf, Reykjavik (IS)

( * ) Notice: Subject to any disclaimer, the term of this patent is extended or adjusted under 35 U.S.C. 154(b) by 809 days.

This patent is subject to a terminal disclaimer.

(21) Appl. No.: 16/913,118

(22) Filed: Jun. 26, 2020

(65) Prior Publication Data

US 2020/0323655 A1 Oct. 15, 2020

Related U.S. Application Data

(63) Continuation of application No. 15/703,061, filed on Sep. 13, 2017, now Pat. No. 10,716,688, which is a
(Continued)

(30) Foreign Application Priority Data

Nov. 7, 2012 (TW) ................. 101141298

(51) Int. Cl.
*A61F 2/60* (2006.01)
*A61F 2/64* (2006.01)
(Continued)

(52) U.S. Cl.
CPC ............. *A61F 2/60* (2013.01); *A61F 2/644* (2013.01); *A61F 2/74* (2021.08);
(Continued)

(58) Field of Classification Search
None
See application file for complete search history.

(56) References Cited

U.S. PATENT DOCUMENTS 2,336,881 A 12/1943 Mortensen
2,465,585 A 3/1949 Ganoe et al.
(Continued)

FOREIGN PATENT DOCUMENTS

CN 1125976 A 7/1996
DE 202005021906 U1 6/2011
(Continued)

OTHER PUBLICATIONS

"Medic OFM2-HD Knee Available with 275 lb. Weight Limit", The O&P Edge, Oandp.com, Dec. 2008, 3 Pages.
(Continued)

*Primary Examiner* — Brian A Dukert
*Assistant Examiner* — Melissa A Hoban
(74) *Attorney, Agent, or Firm* — Workman Nydegger

(57) ABSTRACT

A prosthetic system includes a prosthetic knee having a controller and a hydraulic unit pivotally connected to the controller. The hydraulic includes a reserve hydraulic cylinder, a brake hydraulic cylinder, and a hydraulic cylinder having a lower hydraulic compartment. A flow system fluidly connects the hydraulic cylinder, the reserve hydraulic cylinder, and the brake cylinder. The flow system has first and second flow paths in communication with the lower hydraulic compartment and the reserve hydraulic cylinder. The first flow path is in communication with lower hydraulic compartment and the reserve hydraulic cylinder via the brake cylinder. The second flow path bypasses the brake hydraulic cylinder.

19 Claims, 9 Drawing Sheets

Related U.S. Application Data continuation of application No. 14/074,323, filed on Nov. 7, 2013, now Pat. No. 9,770,347.

(51) Int. Cl.
  *A61F 2/50* (2006.01)
  *A61F 2/68* (2006.01)
  *A61F 2/74* (2006.01)

(52) U.S. Cl.
  CPC . *A61F 2002/502* (2013.01); *A61F 2002/5006* (2013.01); *A61F 2002/5016* (2013.01); *A61F 2002/5033* (2013.01); *A61F 2002/5075* (2013.01); *A61F 2002/5084* (2013.01); *A61F 2002/6818* (2013.01)

(56) References Cited

U.S. PATENT DOCUMENTS

| | | | |
|---|---|---|---|
| 3,723,997 | A | 4/1973 | Kolman |
| 3,982,279 | A | 9/1976 | Valenti et al. |
| 4,152,787 | A | 5/1979 | Meggyesy |
| RE31,673 | E | 9/1984 | Blatchford et al. |
| 4,578,083 | A | 3/1986 | Williams |
| 5,062,857 | A | 11/1991 | Berringer et al. |
| 5,746,774 | A | 5/1998 | Kramer et al. |
| 5,888,237 | A | 3/1999 | Shiraishi et al. |
| 5,899,943 | A | 5/1999 | Shiraishi et al. |
| 6,159,248 | A | 12/2000 | Gramnas |
| 6,206,933 | B1 | 3/2001 | Shorter et al. |
| 6,471,664 | B1 | 10/2002 | Campbell et al. |
| 6,673,117 | B1 | 1/2004 | Soss et al. |
| 6,706,074 | B1 | 3/2004 | Chen |
| 7,544,214 | B2 | 6/2009 | Gramnaes |
| RE42,903 | E | 11/2011 | Deffenbaugh et al. |
| 8,268,012 | B1 | 9/2012 | Cheng et al. |
| 2003/0050712 | A1 | 3/2003 | Shen |
| 2005/0027370 | A1* | 2/2005 | Chen ................... A61F 2/644 623/44 |
| 2006/0259153 | A1 | 11/2006 | Harn et al. |
| 2007/0173953 | A1 | 7/2007 | Imakita et al. |
| 2007/0208431 | A1 | 9/2007 | Bisinger et al. |
| 2008/0281427 | A1 | 11/2008 | Shen |
| 2010/0100197 | A1 | 4/2010 | Kremser et al. |
| 2011/0098828 | A1 | 4/2011 | Balboni et al. |
| 2011/0270415 | A1 | 11/2011 | Chen et al. |
| 2012/0150318 | A1 | 6/2012 | Chabloz |
| 2012/0310372 | A1 | 12/2012 | Omarsson et al. |
| 2013/0085580 | A1* | 4/2013 | Wu ................... A61F 2/644 623/43 |
| 2013/0204395 | A1 | 8/2013 | Gramnaes |

FOREIGN PATENT DOCUMENTS

| | | | |
|---|---|---|---|
| EP | 1166726 | A1 | 1/2002 |
| EP | 1570817 | A1 | 9/2005 |
| EP | 2478875 | A2 | 7/2012 |
| GB | 2270473 | A | 3/1994 |
| TW | 564742 | U | 12/2003 |
| WO | 2009/066055 | A2 | 5/2009 |
| WO | WO-2014016424 | A1 * | 1/2014 ............... A61F 2/64 |

OTHER PUBLICATIONS

"The Light Construction of the OFM2 Aids Energy-Efficient Movement", Medi OFM2, Youtube, Published Oct. 11, 2012.

International Search Report from International PCT Application No. PCT/US2015/016075, dated May 19, 2015.

\* cited by examiner

ADJUSTABLE PROSTHESIS LEG

BACKGROUND OF THE INVENTION

Field of Invention

The invention relates to an adjustable below-the-knee prosthetic leg, and more particularly to an adjustable below-the-knee prosthetic leg that allows a user to climb up or go down the stairs or walk on uneven ground easily without losing balance.

Description of the Related Art

For those who experience amputation due to serious trauma or lesion or for those having congenital limb deficiencies, through the reconstruction of a prosthetic limb, appearance and functions that are comparable to those of a common person can be attained. Especially for those who lose the leg below the knee, besides an essential artificial foot, what's most important is a below-the-knee prosthetic leg connecting the thigh and the artificial foot.

Referring to FIG. 1A or FIG. 1B, a conventional below-the-knee prosthetic leg, which is connected between a thigh 1a and an artificial foot 2a, generally comprises a controller 3a, a connecting mechanism 4a, and a knee joint body 5a. The controller 3a is connected to the thigh 1a. One end of the connecting mechanism 4a is pivotally connected to the controller 3a, and the other end is pivotally connected to a piston structure 51a inside the knee joint body 5a. Furthermore, the controller 3a is also pivotally connected to the knee joint body 5a.

The knee joint body 5a has a hydraulic cylinder 50a provided therein. The piston structure 51a is provided inside the hydraulic cylinder 50a. The connecting mechanism 4a is connected to the piston structure 51a. The piston structure 51a divides the hydraulic cylinder 50a into an upper hydraulic compartment 52a and a lower hydraulic compartment 53a. In addition, a flow path 54a is provided inside the knee joint body 5a for connecting the upper hydraulic compartment 52a and the lower hydraulic compartment 53a. Thus, when the connecting mechanism 4a drives the piston structure 51a to move up and down, the volumes of the upper hydraulic compartment 52a and the lower hydraulic compartment 53a are changed. In addition, a change in the volumes of the upper hydraulic compartment 52a and the lower hydraulic compartment 53a may also exert an influence on the movement of the connecting mechanism, thereby further affecting the bending of the below-the-knee prosthetic leg.

Referring to FIG. 1A, when a user intends to lift the thigh 1a to take a first step, the knee joint body 5a droops naturally under the action gravity. In such a cases the connecting mechanism 4a stretches and pushes the piston structure 51a to move downwards, the volume of the lower hydraulic compartment 53a is compressed, and a hydraulic liquid in the lower hydraulic compartment 53a is injected into the upper hydraulic compartment 52a through the flow path 54a. At this time, the artificial foot 2a does not touch the ground, and thus is not affected by a reactive force; therefore, the knee joint body 5a can rotate freely along with the thigh 1a.

Referring to FIG. 1B, when the user steps on the ground with the artificial foot 2a the connecting mechanism 4a is bent and drives the piston structure 51a to move upwards. In this case, the volume of the lower hydraulic compartment 52a decreases. It should be particularly noted that the center of gravity in the user is inevitably located on this foot at this time, so that the knee joint body 5a cannot swing along with the thigh 1a; otherwise, the user may fall down. The reactive force applied on the artificially foot 2a by the ground contributes to this effect, because the reactive force may be transferred to the piston structure 51a, such that the piston structure 51a is fixed at a position until the artificial foot 2a leaves the ground again and the gravity center of the user is moved to the other foot. However, what is described above is the situation of walking on even ground. In the case of climbing up or going down the stairs or walking on uneven ground, it is required that the body weight can be supported before the thigh 1a and the artificial foot 2a are stretched in a straight line. That is, a mechanism is required through which the volumes of the hydraulic liquid in the upper hydraulic compartment 52a and the lower hydraulic compartment 53a remain the same when the below-the-knee prosthetic leg is bent. Otherwise, the user may lose balance and fall down. To overcome this difficulty, many advanced below-the-knee prosthetic legs are available on the market, for example, Taiwan Patent Publication No. 564742 and EU Patent Publication No. 2478875. However, the former, due to design mistakes, cannot practically fully satisfy the requirements of a user for climbing up or going down the stairs and walking on uneven ground. The latter depends on a large amount of electronic sensing devices, which increases the cost; and the electronic elements are of low reliability and are not water-proof, which fails to meet the requirements of the industry and the users for prosthetic legs.

Therefore, in order to improve the above shortcomings, the present invention, which is reasonably designed, is made by the inventor through intense research and application of academic principles.

SUMMARY OF THE INVENTION

The present invention mainly aims to provide an adjustable below-the-knee prosthetic leg, which allows a user to climb up or go down the stairs and walk on uneven ground without falling down due to loss of balance, and provide angles for pivotally connecting elements, thereby enabling the user to move more easily.

To achieve the objective, the present invention provides an adjustable below-the-knee prosthetic leg which is connected between a thigh and an artificial foot, comprising; a controller provided with a first pivoting portion and a second pivoting portion, where the controller is connected to the thigh; a hydraulic unit provided with a third pivoting portion, a hydraulic cylinder, a reserve hydraulic cylinder, a brake hydraulic cylinder, an adjust-initiating compartment, and a flow system, where the hydraulic unit is pivotally connected to the second pivoting portion, and the hydraulic cylinder, the reserve hydraulic cylinder, and the brake hydraulic cylinder are in communication with each other through the flow system; a connecting mechanism which is pivotally connected to the first pivoting portion and extends into the hydraulic cylinder of the hydraulic unit; and a shell which is pivotally connected to the third pivoting portion and presses against the adjust-initiating compartment, where a horizontal angle formed between the second pivoting portion and the third pivoting portion is 40 to 60 degrees, and the shell is further connected to the artificial foot.

The present invention has the following beneficial effects. The brake valve of the present invention closes the flow path inside the brake hydraulic cylinder when a user bends the thigh and the artificial foot, and transfers the user's center of gravity onto the below-the-knee prosthetic leg, so that volume of the hydraulic liquid in the hydraulic cylinder remains the same, thereby ensuring that the user will not fall down due to loss of balance. In addition, the angle formed between the second pivoting portion and the third pivoting portion allows the user to move freely like a common person.

The following detailed description and drawings relevant to the present invention may be referenced for further understanding the features and technical contents of the present invention. However, the accompanying drawings are provided merely for reference and description and are not intended to limit the present invention.

LIST OF MAIN REFERENCE NUMERALS

Figure 1A:
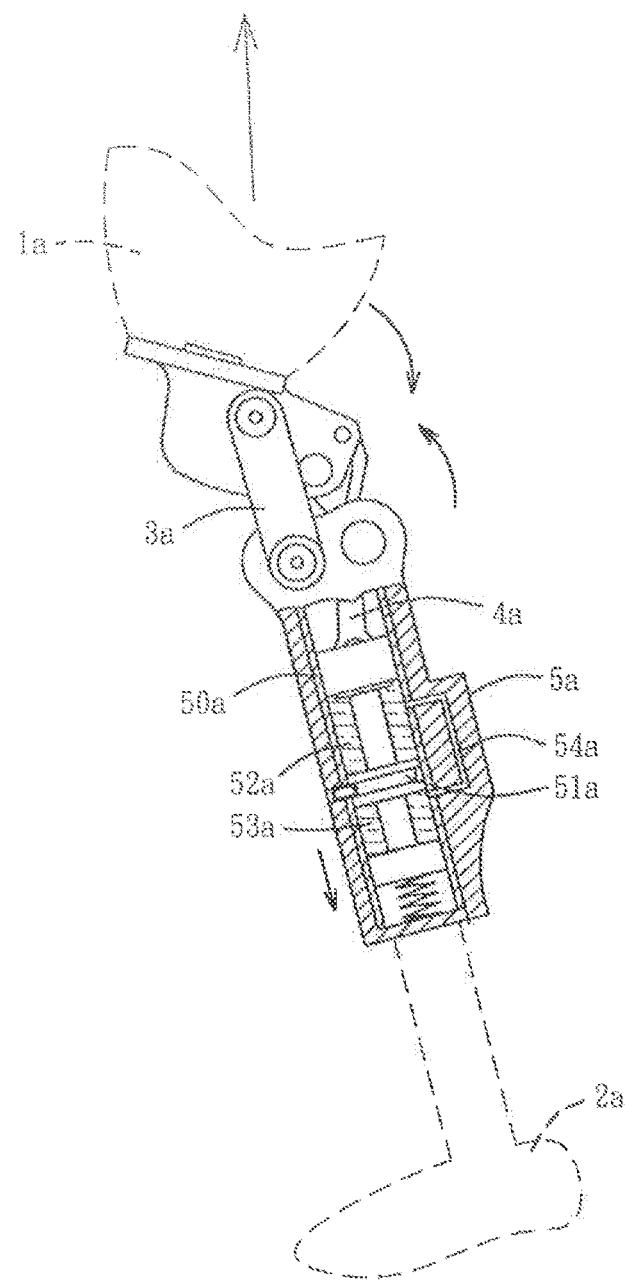
FIG. 1A is a decomposition diagram (1) of an action of a conventional below-the-knee prosthetic leg.
Figure 1B:
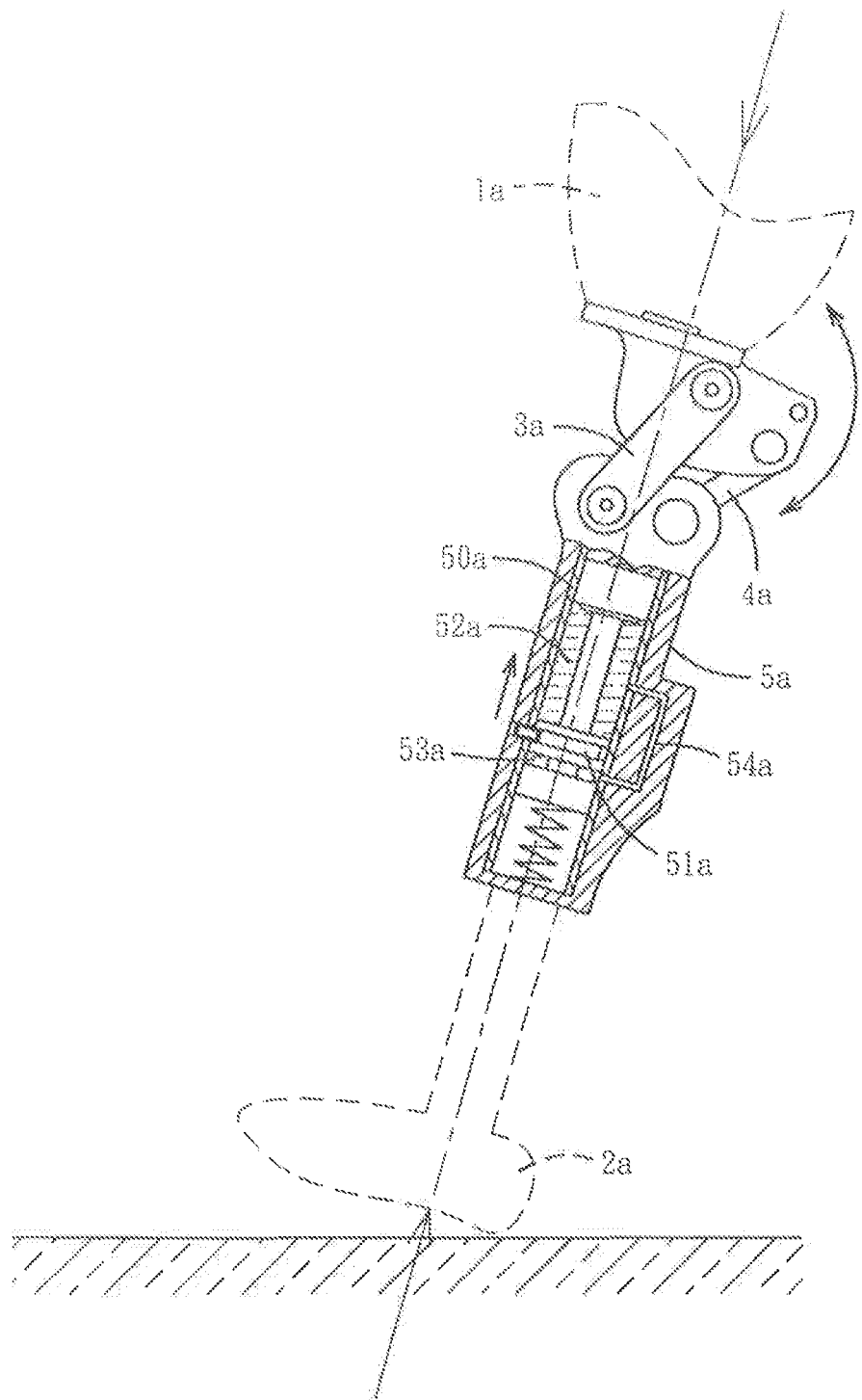
FIG. 1B is a decomposition diagram (2) of the action of the conventional below-the-knee prosthetic leg.

1a Thigh
2a Artificial foot
3a Controller
4a Connecting mechanism
5a Knee joint body
50a Cylinder
51a. Piston structure
52a Upper hydraulic compartment
53a. Lower hydraulic compartment
54a Flow path
A Thigh
B Artificial foot
1 Controller
11 Plate
12 First joining portion
13 Stop block
131 First fixing hole
14 First pivoting portion
141 First rotating shaft
15 Second pivoting portion
151 Second rotating shaft
2 Connecting mechanism
21 Connecting rod
211 Fourth pivoting portion
212 Fourth rotating shaft
22 Piston rod
221 Head end
222 Tail end
223 First piston cup
224 First ring
225 Second piston cup
3 Hydraulic unit
31 Second fixing hole
311 Securing screw
32 Hydraulic cylinder
321 First pressing surface
322 Upper hydraulic compartment
323 Lower hydraulic compartment
33 Reserve hydraulic cylinder
331 Third piston cup
332 Auxiliary elastic body
333 Fourth piston cup
334 Second ring
34 Brake hydraulic cylinder
341 First compartment
3411 Third ring
3412 Gap
342 Second compartment
3421 Fourth ring
343 First spring
344 Block valve
3441 First channel
345 Second spring
346 Adjusting valve
3461 First guiding surface
3462 Second guiding surface
3463 Second channel
347 Brake-initiating valve
3471 Stop portion
3472 Fifth ring
348 Stopper
35 Flow system
351 First flow path
3511 Third screw hole
3512 Second pressing surface
3513 First valve needle
3514 First screw nut portion
3515 First conical surface
3516 Sixth ring
352 Second flow path.
3521 Fourth screw hole
3522 Third pressing surface
3523 Second valve needle
3524 Second conical surface
3525 Second screw nut portion
3526 Fourth ring
36 Third pivoting portion
361 Third rotating shaft
37 Adjust-initiating compartment
371 Elastic element
4 Shell
41 Gap
42 First screw hole
43 First adjusting screw
44 Second screw hole
45 Second adjusting screw
46 Second joining portion

DETAILED DESCRIPTION OF THE PREFERRED EMBODIMENTS

Figure 2:
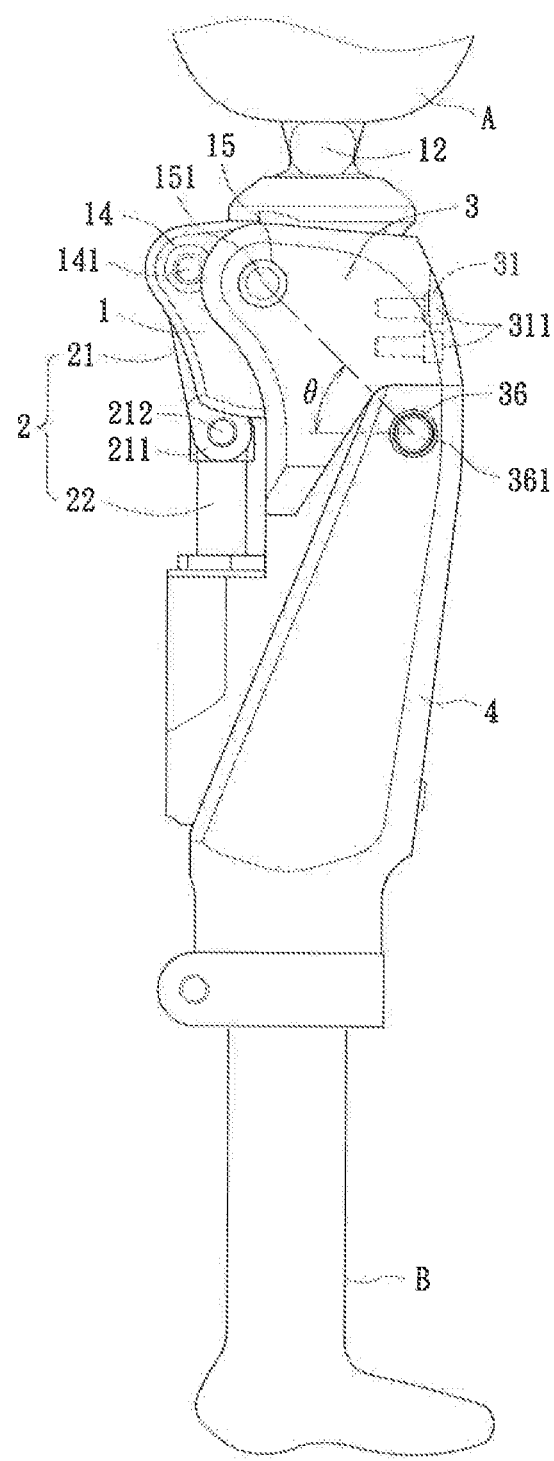
FIG. 2 is a left side view of an adjustable below-the-knee prosthetic leg according to the present invention.
Figure 3:
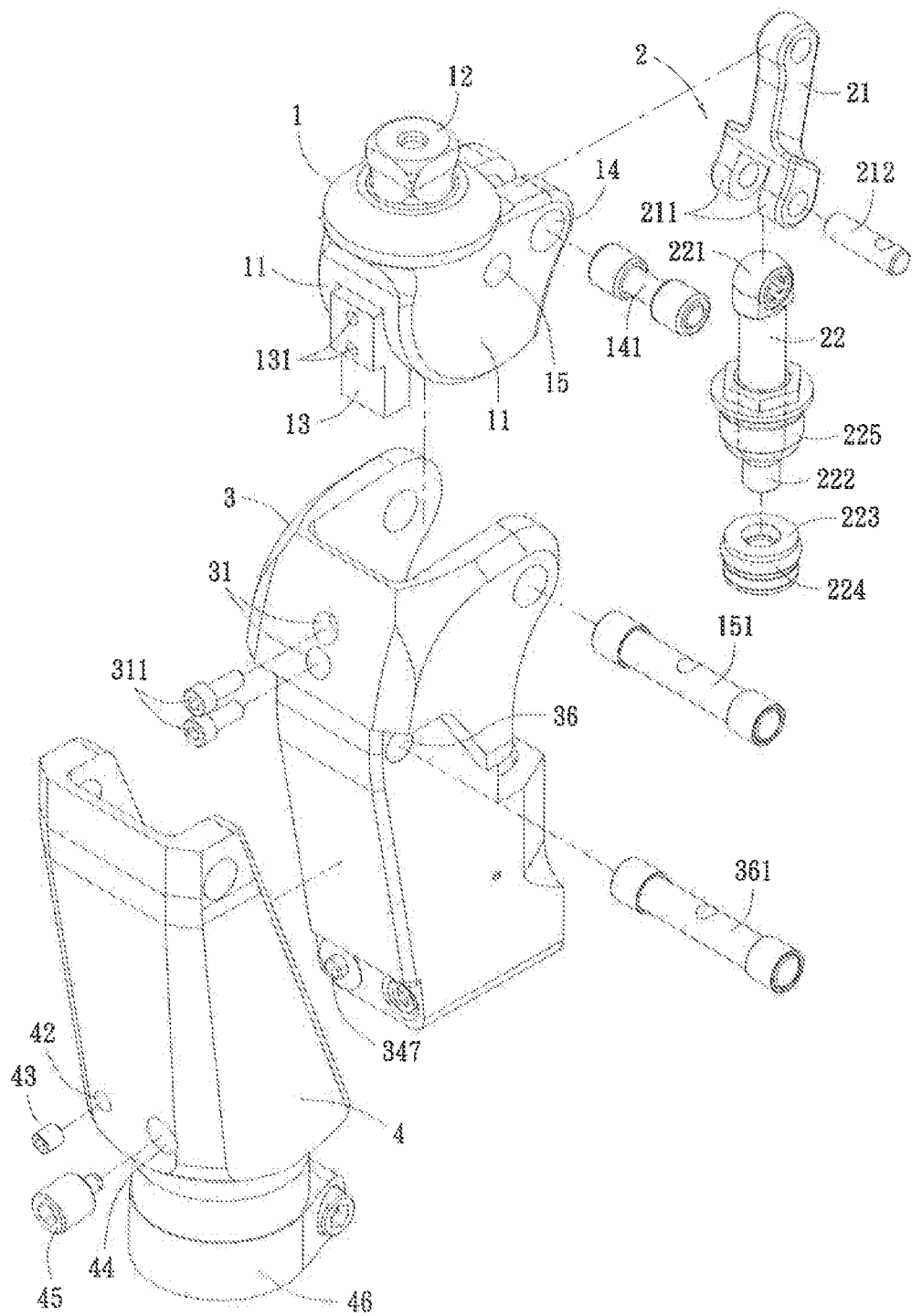
FIG. 3 is an exploded view of the adjustable below-the-knee prosthetic leg according to the present invention.

Referring to FIGS. 2 to 3, the present invention provides an adjustable below-the-knee prosthetic leg which is connected between a thigh A and an artificial foot B. The below-the-knee prosthetic leg comprises a controller 1, a connecting mechanism 2, a hydraulic unit 3, and a shell 4.

The controller 1 is formed by two connected plates 11, where a first joining portion 12 is provided at a junction thereof for being joined to the thigh A. A stop block 13 is sandwiched between the two plates 11. The stop block 13 has two first fixing holes 131 thereon. The two plates 11 are connected into one piece, and provided with a first pivoting portion 14 and a second pivoting portion 15, where the first pivoting portion 14 and the second pivoting portion 15 are both formed by two sets of through holes in the two plates 11. The connecting mechanism 2 is formed by a connecting rod 21 and a piston rod 22 that are pivotally connected to each other. The first pivoting portion 14 is pivotally provided with a first rotating shaft 141 pivoted to one end of the connecting rod 21. The other end of the connecting rod 21 is provided with a fourth pivoting portion 211 formed by two clamp blocks having a through hole, which is used for pivotally connecting to the piston rod 22.

Figure 4:
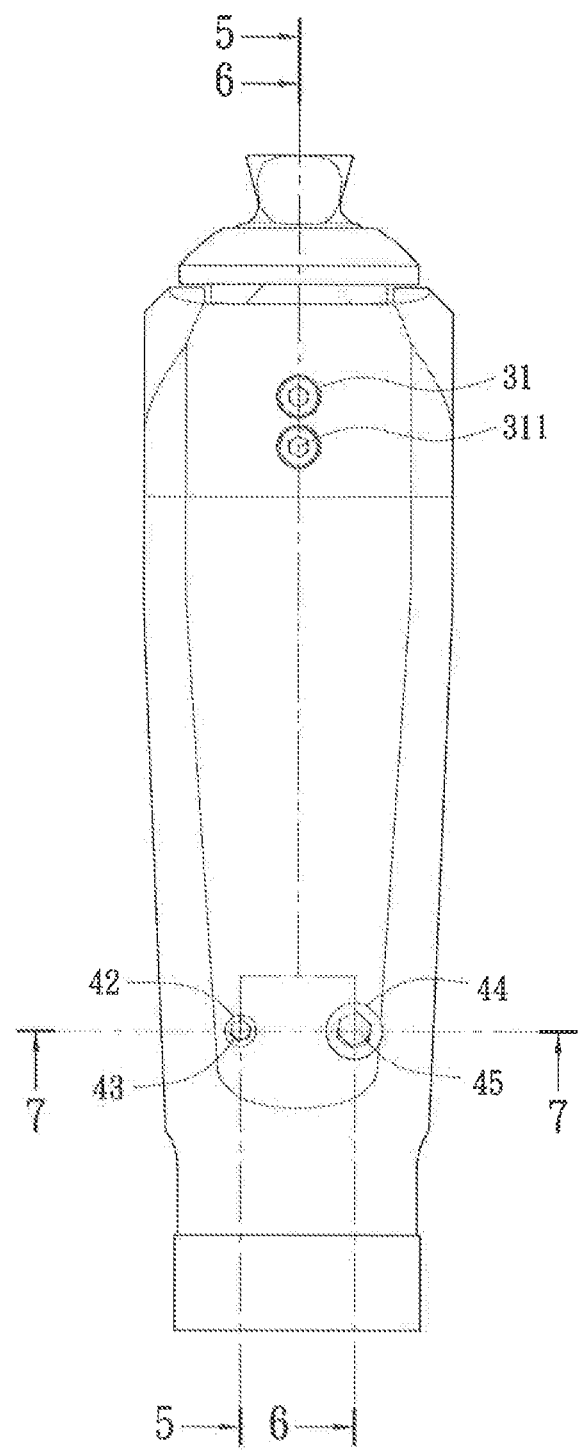
FIG. 4 is a front view of the adjustable below-the-knee prosthetic leg according the present invention.
Figure 5:
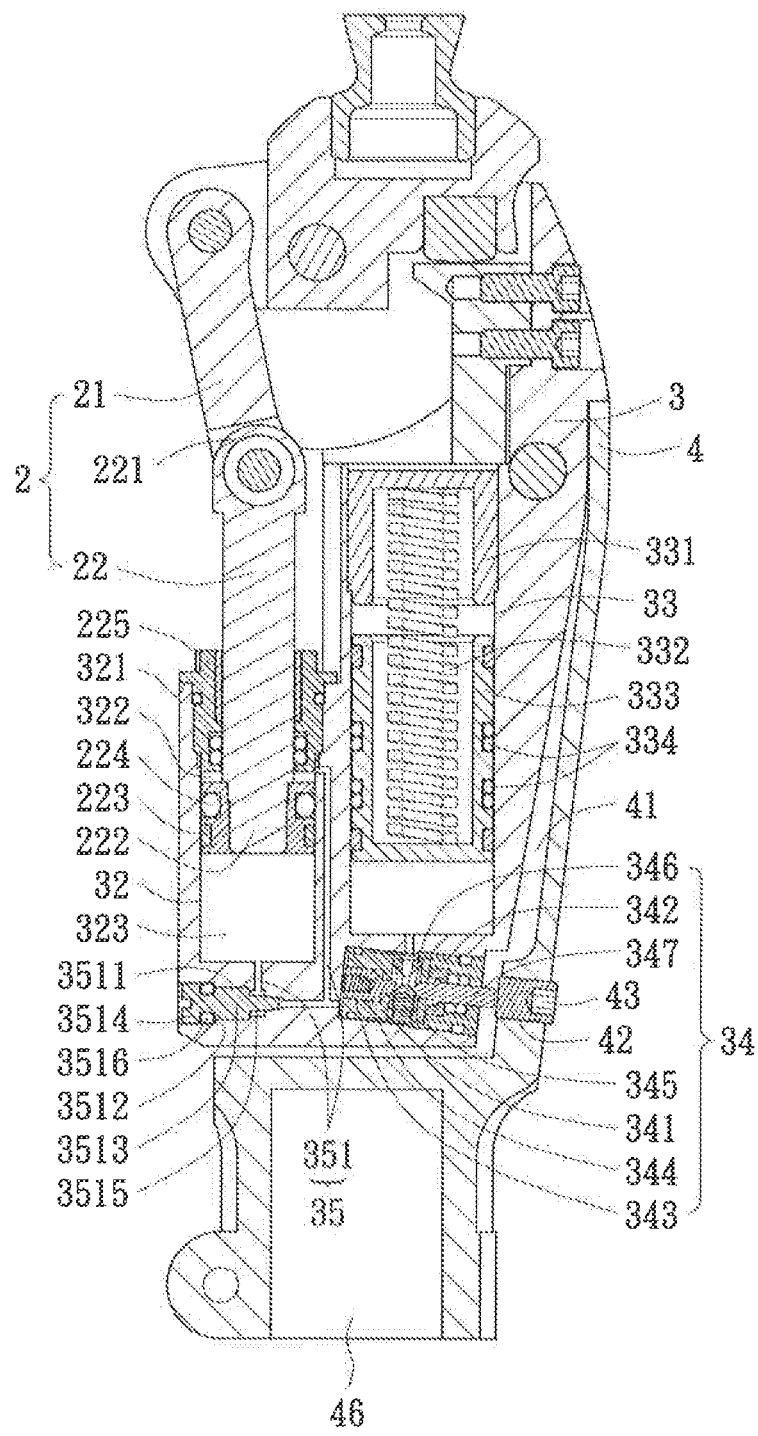
FIG. 5 is a cross-sectional view of the adjustable below-the-knee prosthetic leg according to the present invention shown in FIG. 4 along line 5-5.

FIG. 5 is a cross-sectional view of FIG. 4. Referring to FIGS. 3 to 5, the piston rod 22 has a head end 221 and a tail end 222, where the head end 221 has a through hole, and the head end 221 and the fourth pivoting portion 211 are pivotally connected by a fourth rotating shaft 212. Thus, when the controller 1 is applied with an external force and rotates, the controller drives the connecting mechanism 2 formed by the connecting rod 21 and the piston rod 22 to stretch or bend. The tail end 222 of the piston rod 22 extends into the hydraulic unit 3 and is sleeved with a first piston cup 223. The first piston cup 223 is a hollow cylindrical cup with an opening at one end, on which a first ring 224 is sleeved. In addition, a second piston cup 225 is further provided between the head end 221 and the first piston cup 223, where the second piston cup 225 is a hollow cylindrical cup with openings on both ends, and is movably sleeved on the piston rod 22, so that the first piston cup 223 and the second piston cup 225 may be used to cause the hydraulic liquid in each hydraulic cylinder to flow when the connecting mechanism 2 is moved.

The hydraulic unit 3 has a second rotating shaft 151 extending through two sides at a position close to the top and has two second fixing holes 31 on a front side. The second rotating shaft 151 is pivotally connected to the second pivoting portion 15 of the controller 1, and two securing screws 311 are additionally provided for locking the first fixing holes 131 on the controller and the second fixing holes 31. The hydraulic unit 3 is provided with several hydraulic cylinder chambers and a flow path, including, a hydraulic cylinder 32, a reserve hydraulic cylinder 33, a brake hydraulic cylinder 34, and a flow system 35. The connecting mechanism 2 extends to the hydraulic cylinder 32. The hydraulic cylinder 32 has an eternal first pressed surface 321, and the second piston cup 225 on the piston rod 22 presses against the first pressed surface 321. Therefore, when the connecting mechanism 2 is moved, only the first piston cup 223 sleeved at and fixed to the tail end 222 may move up and down and divide the hydraulic cylinder 32 into an upper hydraulic compartment 322 and a lower hydraulic compartment 323.

Referring to FIGS. 2 and 5, when the user stretches the thigh A and transfers the center of gravity as described in the present invention, the controller 1, the hydraulic unit 3, and shell 4 are in a stretched state, the artificial foot B steps on the ground, and the connecting mechanism 2 is bent with the pulling up by the controller 1 and the pushing by a reactive force applied on the artificial foot B by the ground. When the user lifts the thigh A and transfers the center of gravity to the other foot, the below-the-knee prosthetic leg hangs in the air and gravity naturally acts on the artificial foot B and causes the hydraulic unit 3 and shell 4 to move relative to the controller 1. The hydraulic unit 3 may rotate about the second shaft 151 and cause the connecting mechanism 2 to stretch.

When the below-the-knee prosthetic leg is stretched, the volume of the upper hydraulic compartment 322 is compressed as the connecting mechanism 2 is bent, and the volume of the lower hydraulic compartment 323 increases. When the below-the-knee prosthetic leg is bent, the volume of the upper hydraulic compartment 322 increases as the connecting mechanism 2 is stretched, and the volume of the lower hydraulic compartment 323 decreases. The first ring 224 may fill in a gap between the first piston cup 223 and an inner wall of the hydraulic cylinder 32, thereby preventing the hydraulic liquid in the upper hydraulic compartment 322 and the lower hydraulic compartment 323 from flowing therethrough.

Figure 6:
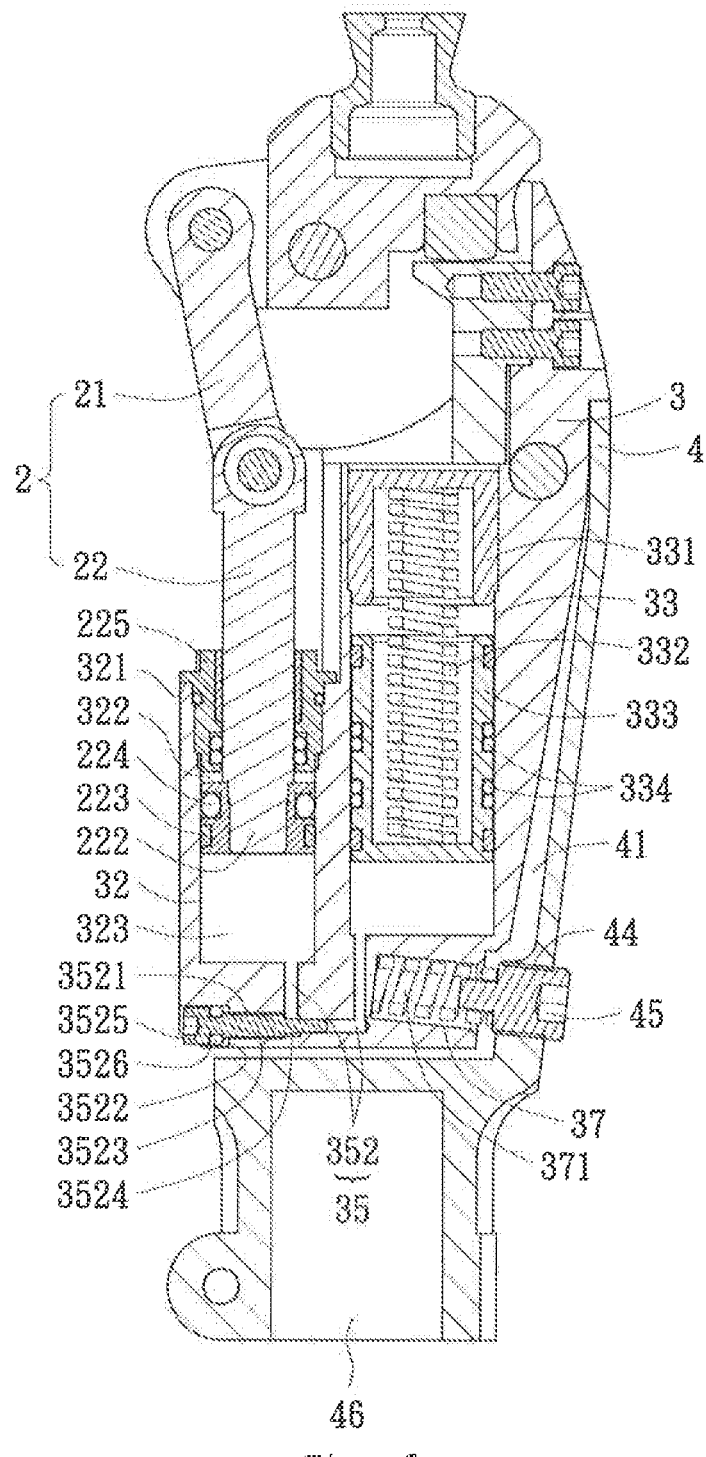
FIG. 6 is a cross-sectional view of the adjustable below-the-knee prosthetic leg according to the present invention shown in FIG. 4 along line 6-6.

Referring to FIGS. 5 and 6, the flow system 35 is divided into a first flow path 351 and a second flow path 352. The upper hydraulic compartment 322 and the lower hydraulic compartment 323 are in communication with the brake hydraulic cylinder 34 through the first flow path 351 in the flow system 35, and the brake hydraulic cylinder 34 is in communication with the reserve hydraulic cylinder 33 through the first flow path 351. Therefore, by controlling the flow of the hydraulic liquid in the brake hydraulic cylinder 34, the movement of the connecting mechanism 2 may be affected, thereby producing a braking effect.

Figure 5A:
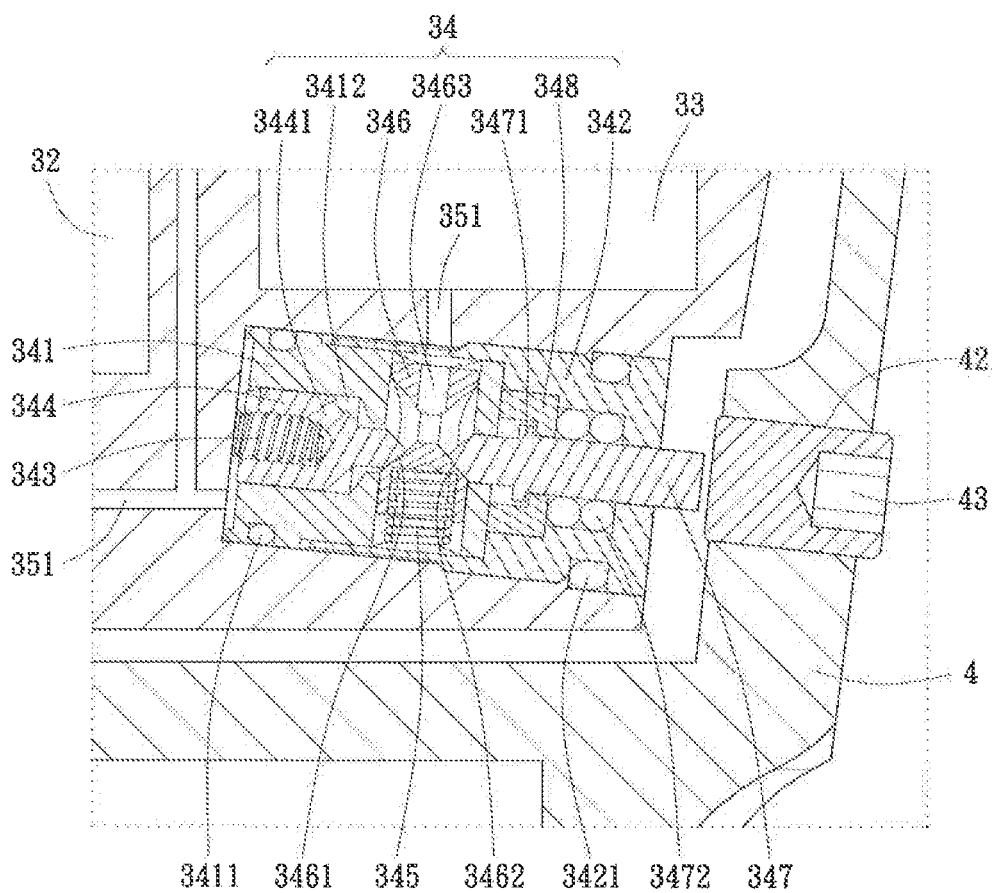
FIG. 5A is a partial enlarged view of the adjustable below-the-knee prosthetic leg according to the present invention.

Referring to FIGS. 5 and 5A, the brake hydraulic cylinder 34 controls the flow of the hydraulic liquid between the hydraulic cylinder 32 and the reserve hydraulic cylinder 33 through an arrangement below. The brake hydraulic cylinder 34 is provided below the reserve hydraulic cylinder 33, and the hydraulic liquid that flows from the reserve hydraulic cylinder 33 through the first flow path 351 to the hydraulic cylinder 32 must pass through the brake hydraulic cylinder 34. The brake hydraulic cylinder 34 has a first compartment 341, a second compartment 342, and a first spring 343 provided therein. The first compartment 341 is provided at a position deeper into the brake hydraulic cylinder 34 than the second compartment 342. One end of the first spring 343 is connected to an inner wall of the brake hydraulic cylinder 34, and the other end presses against a block valve 344. The first spring 343 and the block valve 344 are both located in the first compartment 341. A second spring 345 and an adjusting valve 346 are located between the first compartment 341 and the second compartment 342. One end of the second spring 345 is connected to an inner wall of the second compartment 342, and the other end presses against the adjusting valve 346. The adjusting valve 346 has a first guiding surface 3461 and a second guiding surface 3462 on side surfaces. The first guiding surface 3461 matches a contact end on the block valve 344, the second guiding surface 3462 presses against a brake-initiating valve 347, and the second guiding surface 3462 matches a contact end of the brake-initiating valve 347 opposite to the contact end corresponding to a first adjusting screw 43 that is installed inside the shell 4. The brake-initiating valve 347 is located inside the second compartment 342 and has a circular stop portion 3471. A stopper 348 is positioned between the second compartment 342 and the first compartment 341. The stop portion 3471 is located inside the stopper 348. When the brake-initiating valve 347 is moved, the stopper 348 and the stop portion 3471 press against each other, thereby producing the effect of limiting the brake-initiating valve 347.

A third ring 3411 is sleeved on the first compartment 341, a fourth ring 3421 is sleeved on the second compartment 342, two fifth rings 3472 are sleeved on the brake-initiating valve 347, and the third ring 3411, the fourth ring 3421, and the fifth rings 3472 are all used to prevent the hydraulic liquid in the brake hydraulic cylinder 34 from leaking out. In addition, the hydraulic liquid flowing to the brake hydraulic cylinder 34 through the first flow path 351 flows through a first channel 3441 provided in the block valve 344, a gap 3412 between the first compartment 341 and the block valve 344, a second channel 3463 above the adjusting valve 346, and then through the first flow path 351 to the reserve hydraulic cylinder 33.

In particular, in the brake hydraulic cylinder 34, the spring force of the second spring 345 is greater than that of the first spring 343, Therefore, when the adjusting valve 346 is not pushed by the brake-initiating valve 347, the natural state of the second spring 345 may indirectly cause the first spring 343 to be in a compressed state. When the shell 4 causes the first adjusting screw 43 to push the brake-initiating valve 347, the brake-initiating valve 347 may push the adjusting valve 346 to move downwards and compress the second spring 345. In such a case, the first spring 343 starts to restore, to push the block valve 344 to move towards the adjusting valve 346, and the gap 3412 is closed. At this time, the hydraulic liquid cannot flow from the brake hydraulic cylinder 34 and between the hydraulic cylinder 32 and the reserve hydraulic cylinder 33. That is, the first flow path 351 passing through the brake hydraulic cylinder 34 is blocked, so as to keep the volumes of the upper hydraulic compartment 322 and the lower hydraulic compartment 323 of the hydraulic cylinder 32 unchanged, thereby limiting the movement of the connecting mechanism 2. A second valve needle 3523 is adjusted to control the flow rate to achieve the braking effect. When the first adjusting screw 43 leaves the brake-initiating valve 347, the second spring 345 starts to restore, thereby pushing the brake-initiating valve 347 and the block valve 344 back to their original positions. In this case, the gap 3412 is opened again, and the first flow path 351 is unblocked.

When the first flow path 351 is not blocked by the block valve 344, if the controller 1 pushes the connecting mechanism 2 to drive the first piston cup 223 to compress the lower hydraulic compartment 323, most of the hydraulic liquid in the lower hydraulic cylinder 323 through the brake hydraulic cylinder 34. The reserve hydraulic cylinder 33 has a third piston cup 331, an auxiliary elastic body 332, and a fourth piston cup 333 provided therein. The third piston cup 331 and the fourth piston cup 333 are both hollow cylindrical cups having an opening at one end and having outer surfaces closely adjacent to the inner wall of the reserve hydraulic cylinder 33. The third piston cup 331 is sleeved at one end of the auxiliary elastic body 332 and is fixed to a top of the reserve hydraulic cylinder 33. The fourth piston cup 333 is sleeved at and fixed to the other end of the auxiliary elastic body 332, on which several second rings 334 are sleeved. The elongation and compression of the auxiliary elastic body 332 depends on the force applied to the hydraulic liquid in the reserve hydraulic cylinder 33, and the second rings 334 may be used to prevent the hydraulic liquid from penetration between the third piston cup 331 and the fourth piston cup 333. When the below-the-knee prosthetic leg is bent, to drive the connecting mechanism 2 to push the hydraulic liquid in the lower hydraulic compartment 323 into the reserve hydraulic cylinder 33, the hydraulic liquid pushes the fourth piston cup 333 to compress the auxiliary elastic body 332. However, when the external force applied on the connecting mechanism 2 decreases gradually or vanishes, the compressed auxiliary elastic body 332 restores and pushes the fourth piston cup 333 to feed the hydraulic liquid in the reserve hydraulic cylinder 33 back to the hydraulic cylinder 32, thereby causing the connecting mechanism 2 to be bent again, and thus causing the below-the-knee prosthetic leg to stretch out.

Referring to FIG. 2, the hydraulic unit 3 is provided with a third pivoting portion 36 at two sides below the second fixing holes 31. A line connecting the second pivoting portion 15 and the third pivoting portion 36 forms an angle 0 with the horizontal line, where the angle 0 ranges from 40 to 60 degrees. The third pivoting portion 36 is configured to be pivoted to the shell 4. A third rotating shaft 361 extends through the shell 4 at a position close to the top, and the third rotating shaft 361 is pivoted to the third pivoting portion 36. An inner edge of the shell 4 matches an outer edge of the hydraulic unit 3, and when the artificial foot B is under the action of gravity the hydraulic unit 3 and the shell 4 are caused to bend and hang naturally from the controller 1, a gap 41 exists between the shell 4 and the hydraulic unit 3. When the center of gravity of the user is transferred to the thigh A, such that the shell 4 causes the first adjusting screw 43 to push the brake-initiating valve 347 and the block valve 344 closes the brake hydraulic cylinder 34, the gap 41 is accordingly closed. A bottom of the shell 4 is provided with a second joining portion 46 for being joined to the artificial foot B.

FIG. 6 is another cross-sectional view of FIG. 4. Referring to FIGS. 4 to 6, the adjustable below-the-knee prosthetic leg according to the present invention may be adapted to users with different weights or exercises. The shell 4 has a first screw hole 42 and a second screw 44. The first adjusting screw 43 is screwed into the first screw hole 42. The hydraulic unit 3 has an adjust-initiating compartment 37 corresponding to the second screw hole 44 provided therein. The adjust-initiating compartment 37 is arranged in parallel to the brake hydraulic cylinder 34 and presses against the shell 4. One end of an elastic element 371 is connected to an inner side of the adjust-initiating compartment 37, where the elastic element 371 is a strong elastic body which requires a great external force for elongation or compression. Another end of the elastic element 371 presses against a second adjusting screw 45, and the second adjusting screw 45 is screwed into the second screw hole 44. In this way, the user may rotate the second adjusting screw 45 to determine the elongation and compression of the elastic element 371 and the depth of the gap 41. If the user lifts weights or exercises a lot, the elastic element 371 may be required to produce a higher elastic force. Similarly, when the user has a light weight or exercises little, the elastic element 371 is only required to produce a small elastic force. It should be noted that the restore of the elastic element 371 also enables the first adjusting screw 43 to stop pushing the brake-initiating valve 347, thereby opening the flow path for unblocking the first flow path 351. In addition, the restoring force provided by the second spring 345 in the brake hydraulic cylinder 34 is only sufficient for pushing the block valve 344 and the brake-initiating valve 347 and is insufficient for pushing the shell 4. Therefore, the shell 4 is moved by the elastic element 371 in the adjust-initiating compartment 37.

The first flow path 351 has a third screw hole 3511 extending to the outside of the hydraulic unit 3 below the hydraulic cylinder 32, and the third screw hole 3511 has a second internal pressed surface 3512 and is screwed with a first valve needle 3513 for controlling the flow rate. The first valve needle 3513 is provided with a first screw nut portion 3514, and the first screw nut portion 3514 is clamped in the second pressed surface 3512. The third screw hole 3511 has a first internal conical surface 3515, where the conical surface is located exactly at an intersection where the first flow path 351 connects the lower hydraulic compartment 323 and the brake hydraulic cylinder 34. The shape of a top of the first valve needle 3513 matches that of the first conical surface 3515, and a sixth ring 3516 is sleeved between the first screw nut portion 3514 and the second pressed surface 3512, which may prevent the hydraulic liquid from leaking out.

The invention allows the user to finely adjust the hydraulic cylinder 32 and the reserve hydraulic cylinder 33 independent of the braking effect produced by the first flow path 351. The second flow path 352 may be independently in communication with the hydraulic cylinder 32 and the reserve hydraulic cylinder 33, and a fourth screw hole 3521 extending outside of the hydraulic unit 3 is provided in the second flow path 352 at a position that is parallel to the third screw hole 3511, and has a third internal pressed surface 3522 and is screwed with a second valve needle 3523 for controlling the flow rate. The second valve needle 3523 has a second screw nut portion 3525, and the second screw nut portion 3525 is clamped in the third pressed surface 3522. The fourth screw hole 3521 has a second internal conical surface 3524, and the conical surface is located exactly at an intersection where the second flow path 352 connects the lower hydraulic compartment 323 and the reserve hydraulic cylinder 33. The shape of a top of the second valve needle 3523 matches that of the second conical surface 3524, and there is also a fourth ring 3526 for preventing the hydraulic liquid from leaking out. When the brake hydraulic cylinder 34 is closed, the user may control the flow rate of the hydraulic liquid by adjusting the second screw nut portion 3525, thereby affecting the braking rate.

Referring to FIG. 2, it should be noted that an angle θ formed between a line connecting the centers of the second pivoting portion 15 and the third pivoting portion 36 and the horizontal line ranges from 40 to 60 degrees, and the third pivoting portion 36 is a center of rotation of torque. When the center of gravity is transferred to the thigh A, the artificial foot B steps on the ground and receives a reactive force from the ground; when the torque produced by the reactive force is greater than the elastic force of the elastic element 371, the braking function is started. Such a range of angle is a result obtained from repeated experiments conducted by the inventor. The effect is that, from the time when the heel of the artificial foot B starts to step on the ground (where a reactive force from the ground is applied) to the time when two thirds of the foot steps on the ground, the braking function is started. At this time the center of gravity of the user starts to be transferred to the other foot, and the elastic element 371 and the second spring 345 are required to store, thereby opening the brake-initiating valve 347 for unblocking the flow path between the hydraulic cylinder 32 and the reserve hydraulic cylinder 33. In this way, the below-the-knee prosthetic leg may swing naturally after the center of the gravity is transferred. The angle set between the second pivoting portion 15 and the third pivoting portion 36 affects the movement relationship between the controller 1, the hydraulic unit 3, and the shell 4.

Figure 7:
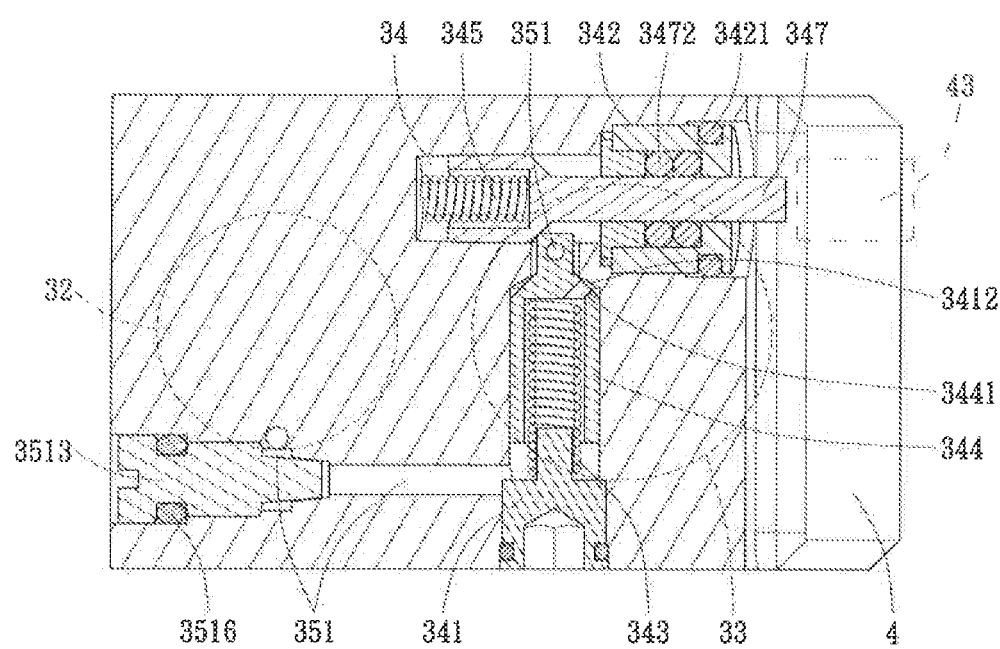
FIG. 7 is a cross-sectional view of the adjustable below-the-knee prosthetic leg according to the present invention shown in FIG. 4 along line 7-7.

FIG. 7 is another cross-sectional view of FIG. 4 and shows another preferential embodiment of this creation. The major difference in structure between this embodiment and the embodiment described above lies in that no adjusting valve 346, stop portion 3471 of the brake-initiation valve 347, and stopper 348 are provided in the brake hydraulic cylinder 34, but the braking effect similar to that in the embodiment described above can still be attained.

When the shell 4 causes the first adjusting screw 43 to push the brake-initiating valve 347, the brake-initiating valve 347 may push and compress the second spring 345. In this case, the block valve 344 may be pushed upwards by the first spring 343 which is in a compressed state originally, thereby closing the gap 3412 between the first channel 3441 and the block valve 344, so that the hydraulic liquid between the hydraulic cylinder 32 and the reserve hydraulic cylinder 33 cannot flow through the first flow path 351.

When the first adjusting screw 43 leaves the brake-initiating valve 347, the previously compressed second spring 345 starts to restore, thereby pushing the brake-initiating valve 347 back to its original position; and the reset brake-initiating valve 347 may press the block valve 344 to compress the first spring 343, and the block valve 344 moves downwards, to open the gap 3412 so that the hydraulic liquid may flow through the first channel 3441.

To sum up, the adjustable below-the-knee prosthetic leg according to the present invention has the following beneficial effects:

1. By setting the brake hydraulic cylinder, when the thigh and the artificial foot are bent relative to each other, the adjustable below-the-knee prosthetic leg of the present invention connected therebetween may support the center of gravity of the user, allowing the user to climb up or go down the stairs or walk on uneven ground without falling down due to loss of balance; in addition, by setting the second adjusting screw, the elastic element, and the adjust-initiating compartment, the force required by initiation of the braking function may be adjusted according to the user's requirements.

2. The angle ranging from 40 to 60 degrees between the second pivoting portion and the third pivoting portion may facilitate the user to walk more naturally and smoothly like a common person.

3. With the cooperation between the second valve needle and the flow system, in the present invention, the amount of the hydraulic liquid passing through the flow system can be finely adjusted, so that the adjustable below-the-knee prosthetic leg according to the present invention may better meet the user's requirements.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

The invention claimed is:

1. A prosthetic knee comprising:
    a controller; and
    a hydraulic unit pivotally connected to the controller, the hydraulic unit including:
        a hydraulic cylinder having a lower hydraulic compartment;
        a brake hydraulic cylinder; and
        a flow system fluidly connecting the hydraulic cylinder and the brake hydraulic cylinder;
    wherein the brake hydraulic cylinder includes a block valve in a first component of the brake hydraulic cylinder and a brake-initiating valve in a second component of the brake hydraulic cylinder;

further comprising a shell pivotally connected to the hydraulic unit and arranged to press against the brake hydraulic cylinder, the brake-initiating valve having a portion extending outwardly from the second component and located along an inside surface of the shell for contact therewith.

2. The prosthetic knee of claim 1, wherein the flow system has first and second flow paths communicating with the lower hydraulic compartment and a reserve hydraulic cylinder, the first flow path being communicating in communication with the lower hydraulic compartment and the reserve hydraulic cylinder via the brake hydraulic cylinder, the first flow path is in fluid with the lower hydraulic compartment, an upper hydraulic compartment, the reserve hydraulic cylinder, and the brake hydraulic cylinder.

3. The prosthetic knee of claim 2, wherein the second flow path bypasses the brake hydraulic cylinder, the second flow path is in fluid communication with the lower hydraulic compartment and the reserve hydraulic cylinder.

4. The prosthetic knee of claim 1, further comprising a connecting mechanism pivotally connected to the controller and extending into the hydraulic cylinder.

5. The prosthetic knee of claim 4, wherein the connecting mechanism includes a connecting rod and a piston rod.

6. The prosthetic knee of claim 4, wherein the controller includes a first pivoting portion and a second pivoting portion.

7. The prosthetic knee of claim 6, wherein the connecting mechanism pivots about the first pivoting portion of the controller.

8. The prosthetic knee of claim 6, wherein the hydraulic unit pivots about the second pivoting portion of the controller.

9. The prosthetic knee of claim 1, wherein each of the block valve and the brake-initiating valve are biased directly against an adjusting valve, the brake hydraulic cylinder adapted to regulate the first flow path from a reserve cylinder to the hydraulic cylinder, the shell is pivotally connected to the brake-initiating valve to urge the brake initiating valve against the adjusting valve.

10. The prosthetic knee of claim 1, wherein the controller includes a joining portion, a first pivoting portion, and a second pivoting portion, each of the first and second pivoting portions disposed at respective fixed locations relative to the joining portion.

11. The prosthetic knee of claim 1, further comprising a prosthetic foot operatively connected to the prosthetic knee.

12. The prosthetic knee of claim 1, further comprising a prosthetic thigh operatively connected to the prosthetic knee.

13. The prosthetic knee of claim 1, wherein the brake hydraulic cylinder has a first compartment, a second compartment, and a first spring, the first spring is biased between the block valve and an inner wall of the first compartment, and a second spring is biased between a wall of the second compartment and an adjusting valve, a spring force of the second spring is greater than a spring force of the first spring.

14. The prosthetic knee of claim 1, wherein the brake-initiating valve has a stop portion and the brake hydraulic cylinder includes a stopper arranged such that when the brake-initiating valve is moved to a predetermined extent, the stopper and the stop portion press against each other to limit movement of the brake-initiating valve.

15. A prosthetic knee comprising:
a controller;
a hydraulic unit pivotally connected to the controller, the hydraulic unit including:
a hydraulic cylinder having upper and lower hydraulic compartments;
a brake hydraulic cylinder having first and second compartments; and
a flow system fluidly connecting the hydraulic cylinder and the brake cylinder; and
a shell pivotally connected to the hydraulic unit and arranged to press against the brake hydraulic cylinder;
wherein the brake hydraulic cylinder includes a block valve in a first component of the brake hydraulic cylinder and a brake-initiating valve in a second component of the brake hydraulic cylinder, each of the block valve and the brake-initiating valve biased directly against an adjusting valve located between the first and second compartments;
wherein the shell has an adjusting screw pivotally connected to the brake-initiating valve to urge the brake initiating valve against the adjusting valve.

16. The prosthetic knee of claim 15, wherein the flow system has first and second flow paths in communication with the lower hydraulic compartment and a reserve hydraulic cylinder, the first flow path being in communication with the lower hydraulic compartment and the reserve hydraulic cylinder via the brake hydraulic cylinder, and the second flow path bypassing the brake hydraulic cylinder.

17. The prosthetic knee of claim 16, wherein the first flow path is in fluid communication with the lower hydraulic compartment, the upper hydraulic compartment, the reserve hydraulic cylinder, and the brake hydraulic cylinder.

18. The prosthetic knee of claim 16, wherein the second flow path is in fluid communication with the lower hydraulic component and the reserve hydraulic cylinder.

19. A prosthetic knee comprising:
a controller; and
a hydraulic unit pivotally connected to the controller, the hydraulic unit including:
a hydraulic cylinder having a lower hydraulic compartment;
a brake hydraulic cylinder; and
a flow system fluidly connecting the hydraulic cylinder and the brake hydraulic cylinder;
wherein the brake hydraulic cylinder includes a block valve in a first component of the brake hydraulic cylinder and a brake-initiating valve in a second component of the brake hydraulic cylinder;
wherein each of the block valve and the brake-initiating valve are biased directly against an adjusting valve having first and second guiding surfaces, the first guiding surface matches a contact end of the block valve, and the second guiding surface matches a contact end of the brake-initiating valve.

\* \* \* \* \*